(12) United States Patent
Ashby et al.

(10) Patent No.: US 7,159,716 B2
(45) Date of Patent: Jan. 9, 2007

(54) EASY CUTTER

(75) Inventors: Mark Ashby, Laguna Nigel, CA (US); Luis R. Urquidi, Laguna Hills, CA (US)

(73) Assignee: Sub-Q, Inc., San Clemente, CA (US)

( * ) Notice: Subject to any disclaimer, the term of this patent is extended or adjusted under 35 U.S.C. 154(b) by 47 days.

(21) Appl. No.: 09/843,496

(22) Filed: Apr. 25, 2001

(65) Prior Publication Data
US 2002/0002889 A1    Jan. 10, 2002

Related U.S. Application Data

(60) Provisional application No. 60/200,702, filed on Apr. 28, 2000.

(51) Int. Cl.
*A61B 19/00* (2006.01)

(52) U.S. Cl. .................... 206/438; 604/15; 606/191

(58) Field of Classification Search .............. 83/599, 83/692, 693, 694, 13, 394, 542, 671, 440, 83/467.1, 564, 566, 582, 588, 589, 597, 598, 83/684, 620, 698.31, 917, 695; 604/200, 604/204, 385, 369, 15; 30/29, 279.2, 253, 30/229, 231; 606/191; 206/570, 223, 438
See application file for complete search history.

(56) References Cited

U.S. PATENT DOCUMENTS

| | | | |
|---|---|---|---|
| 685,212 A | 10/1901 | Knowlton | |
| 1,125,577 A | 1/1915 | Manypeny | |
| 1,373,053 A | 3/1921 | Christensen | |
| 1,696,442 A * | 12/1928 | Messmer, Jr. ................ | 83/597 |
| 1,962,737 A | 6/1934 | Gutmann | |
| 2,076,436 A * | 4/1937 | Nelson ......................... | 83/917 |
| 2,101,458 A * | 12/1937 | Sachtleben .................. | 83/588 |
| 2,258,843 A | 10/1941 | Brown | |
| 2,370,319 A * | 2/1945 | Lippincott ................... | 83/597 |
| 2,847,759 A | 8/1958 | Jones | |
| 2,874,776 A * | 2/1959 | Hooe .......................... | 83/693 |
| 4,124,937 A | 11/1978 | Gaughf, Jr. | |
| 4,573,576 A * | 3/1986 | Krol .......................... | 604/104 |
| 4,644,649 A * | 2/1987 | Seaman et al. .............. | 83/588 |
| 4,869,143 A | 9/1989 | Merrick et al. | |
| 5,005,458 A | 4/1991 | Merrick | |
| 5,052,258 A | 10/1991 | Hunter | |
| 5,291,813 A | 3/1994 | Blumenthal et al. | |
| 5,392,917 A | 2/1995 | Alpern et al. | |
| 5,507,279 A | 4/1996 | Fortune et al. ......... | 128/200.26 |
| 6,012,586 A | 1/2000 | Misra | |
| 6,086,607 A | 7/2000 | Cragg et al. ................ | 606/213 |
| 6,116,132 A | 9/2000 | Kamijo | |
| 6,162,192 A | 12/2000 | Cragg et al. | |
| 6,315,753 B1 * | 11/2001 | Cragg et al. ................. | 604/15 |
| 6,342,069 B1 * | 1/2002 | Deac et al. ................. | 623/2.1 |

(Continued)

OTHER PUBLICATIONS

PCT International Preliminary Examination Report for PCT/US01/13569, dated Sep. 5, 2003.

*Primary Examiner*—Stephen Choi
(74) *Attorney, Agent, or Firm*—Miller Matthias & Hull

(57) ABSTRACT

A cutting device is described having a base with an opening with cutting edges, and a flap articulated with respect to the base, the flap having a shape corresponding to the opening and cutting edges corresponding to the cutting edges of the opening. The cutting device is preferably provided as part of a kit for preparing and delivering hemostatic material to a patient.

6 Claims, 7 Drawing Sheets

U.S. PATENT DOCUMENTS 6,547,806 B1 * 4/2003 Ding .......................... 606/213

2002/0151952 A1 * 10/2002 Perouse ..................... 623/1.11

* cited by examiner

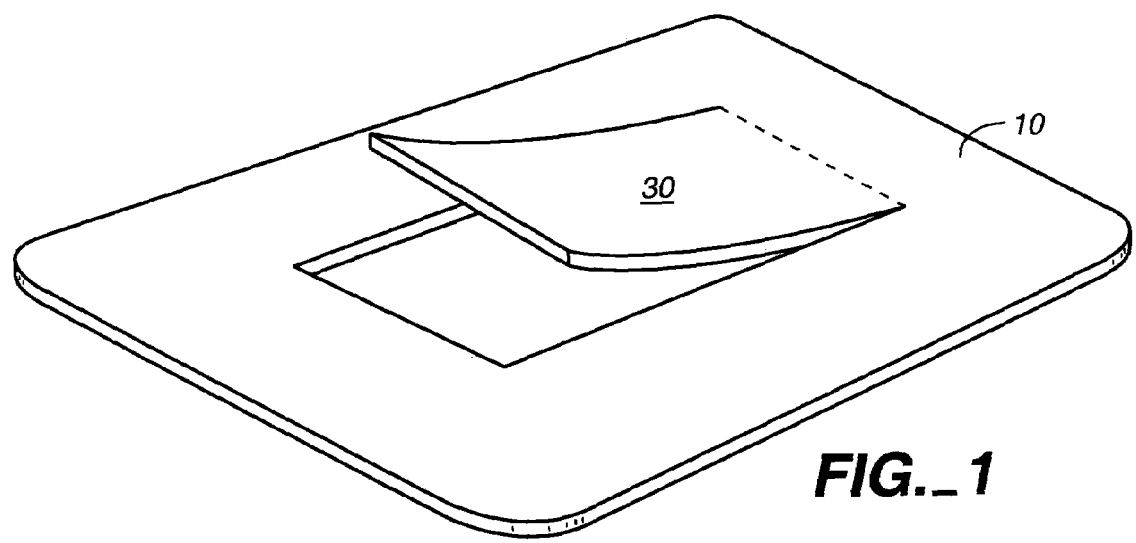
FIG._1
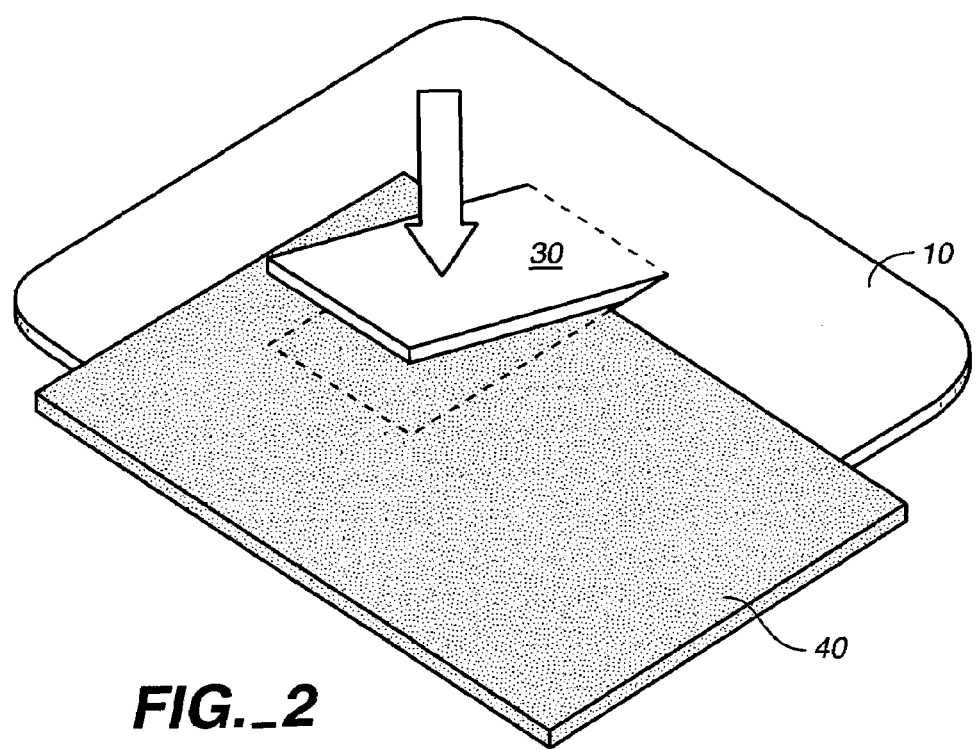
FIG._2

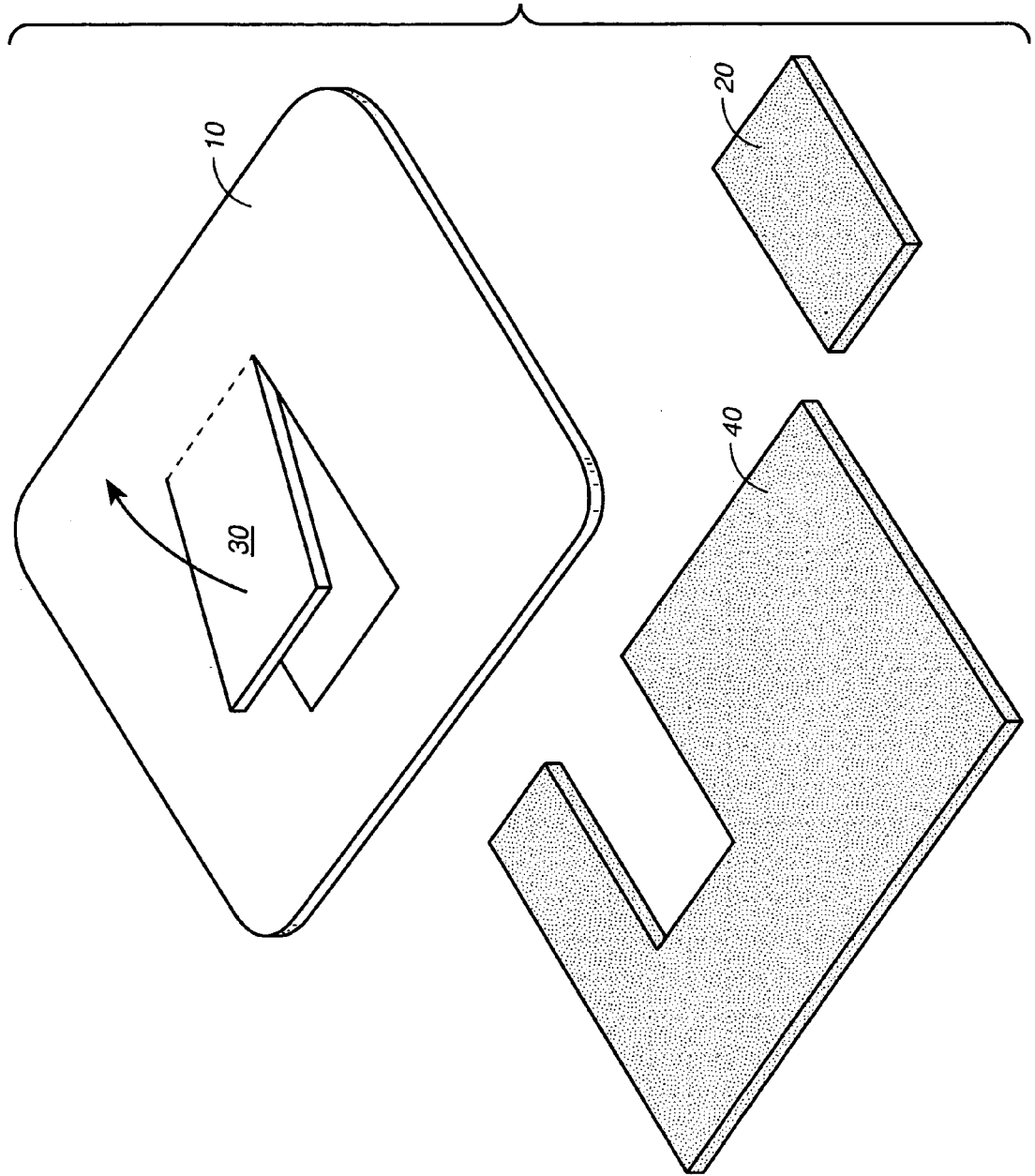

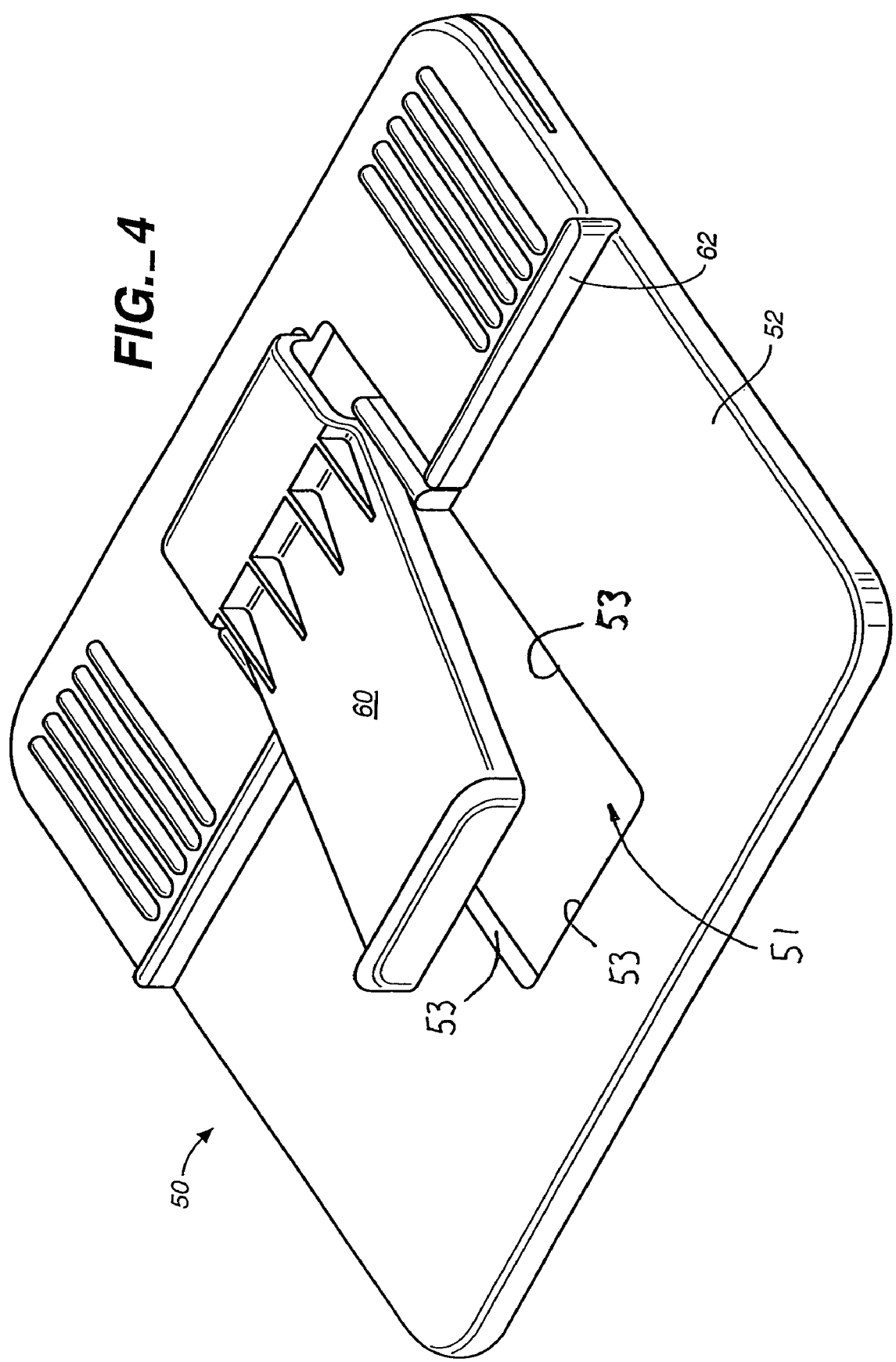
FIG._4

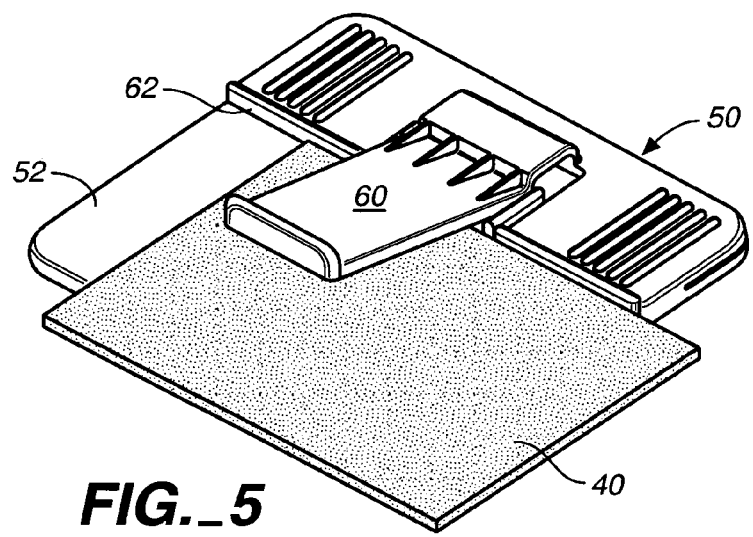
FIG._5
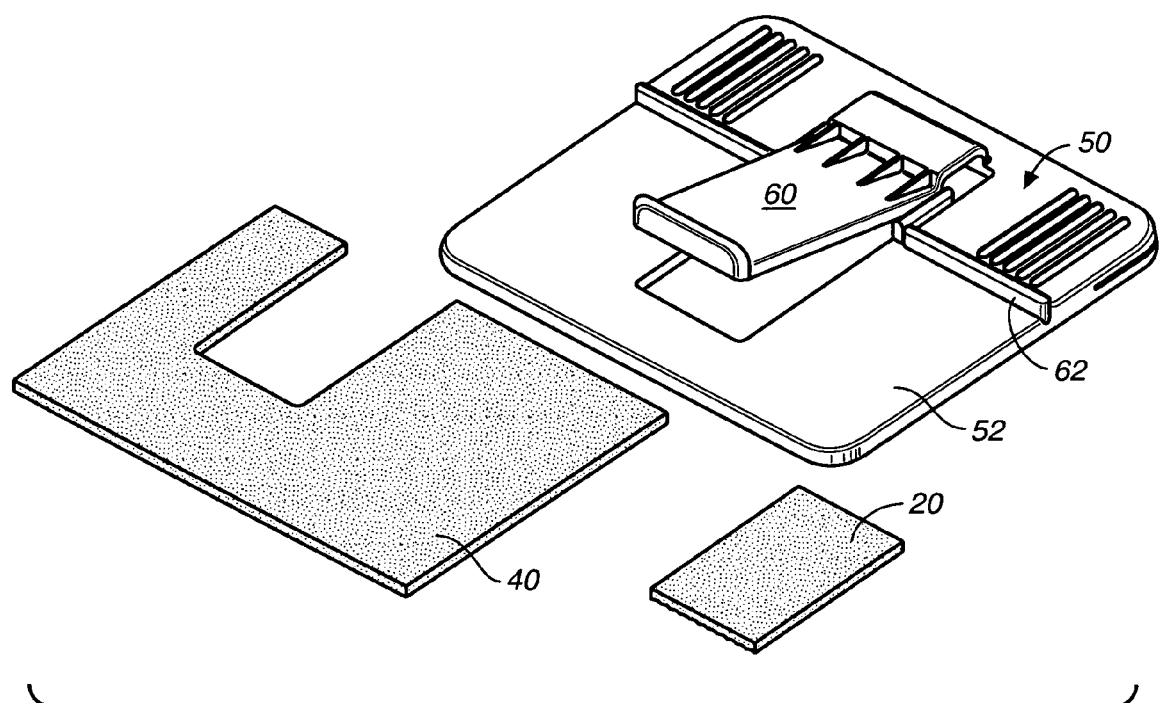
FIG._6

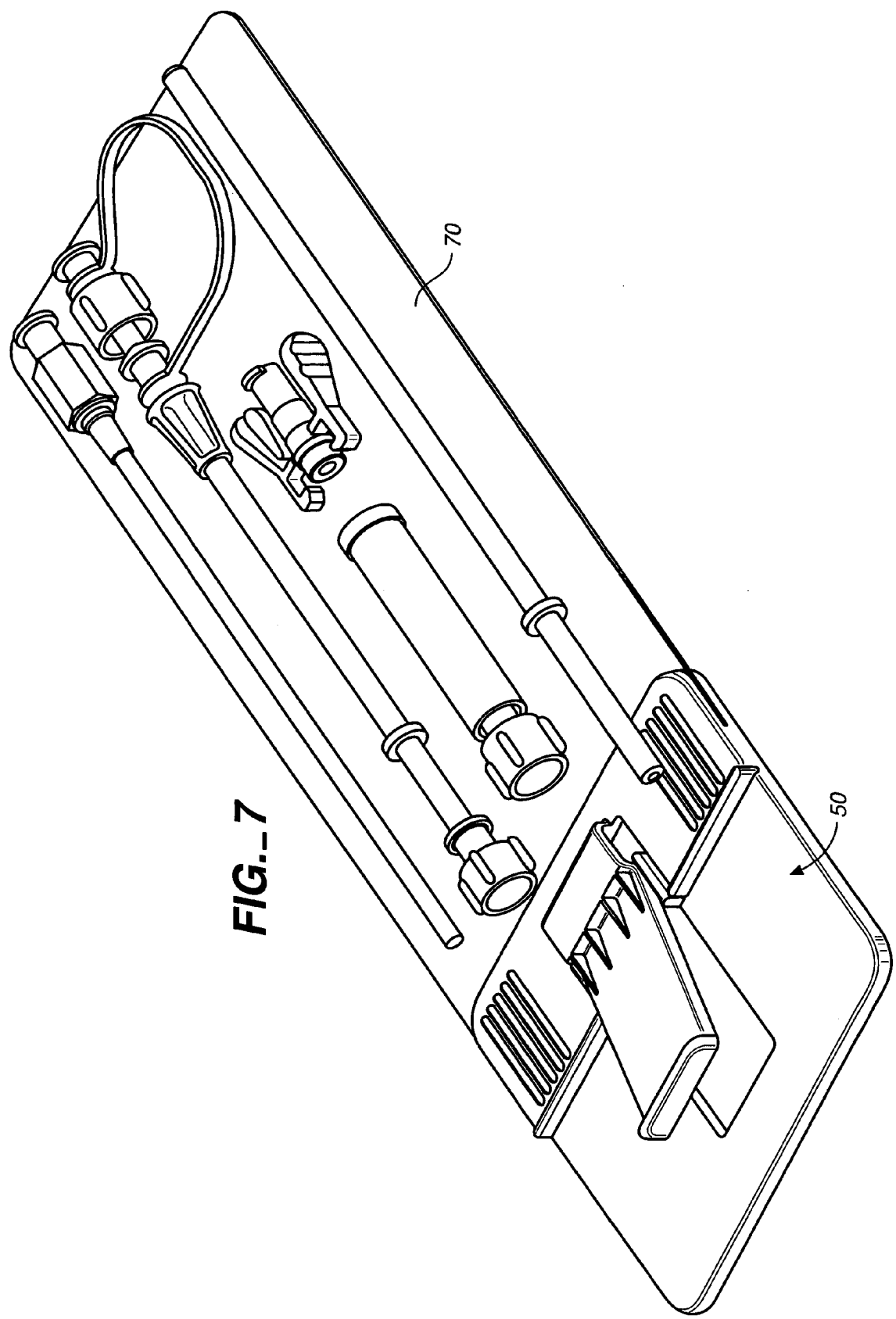
FIG._7

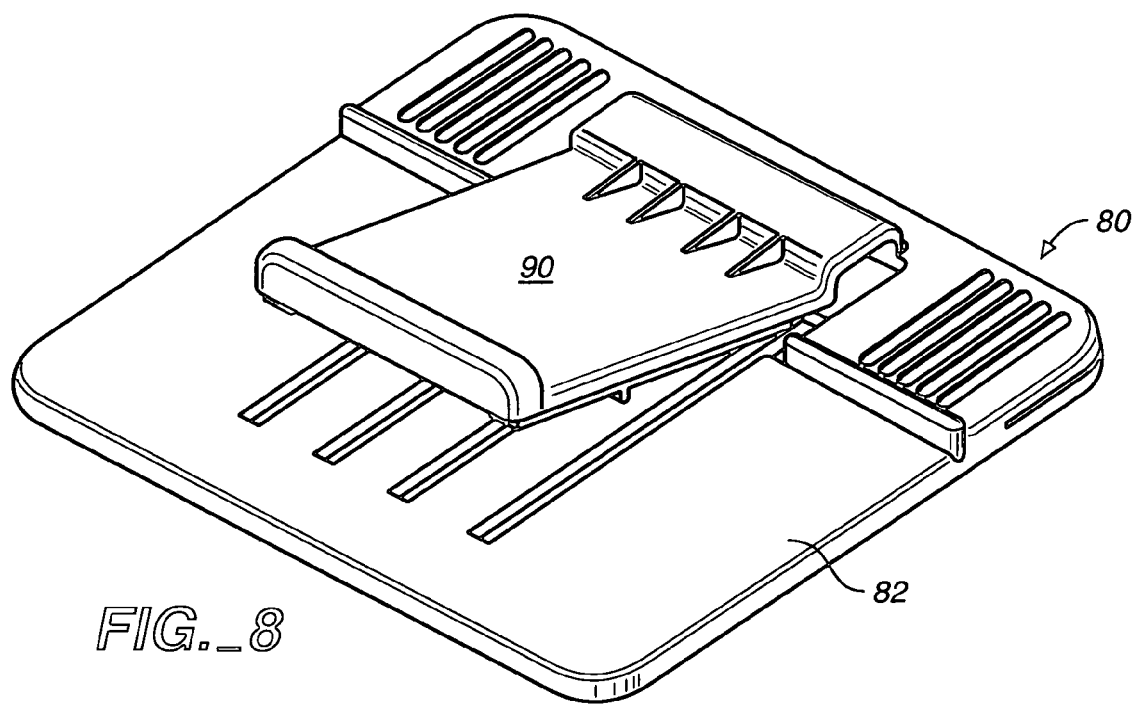
FIG._8
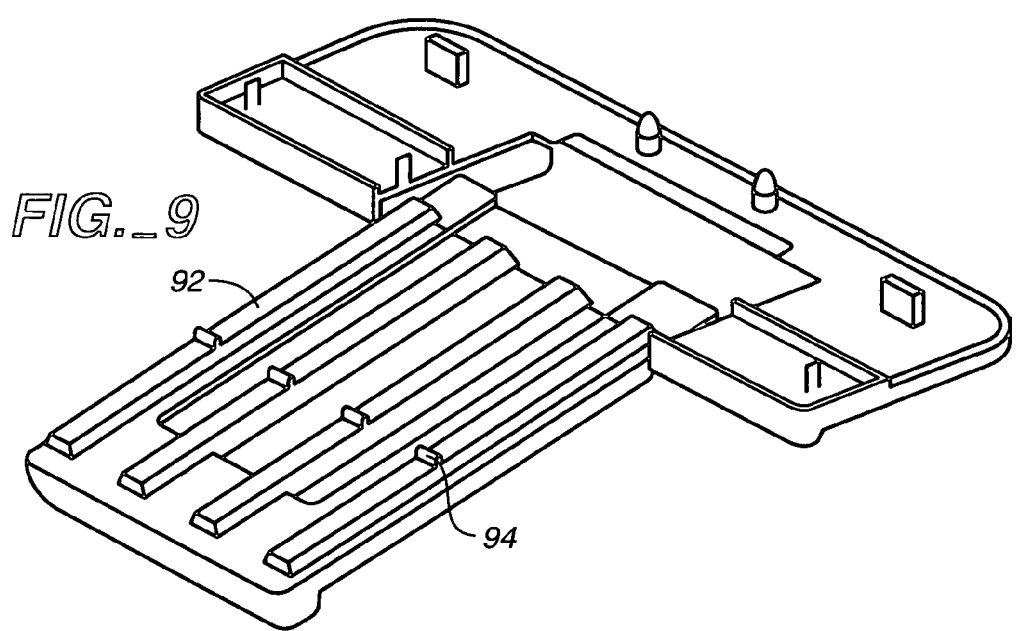
FIG._9

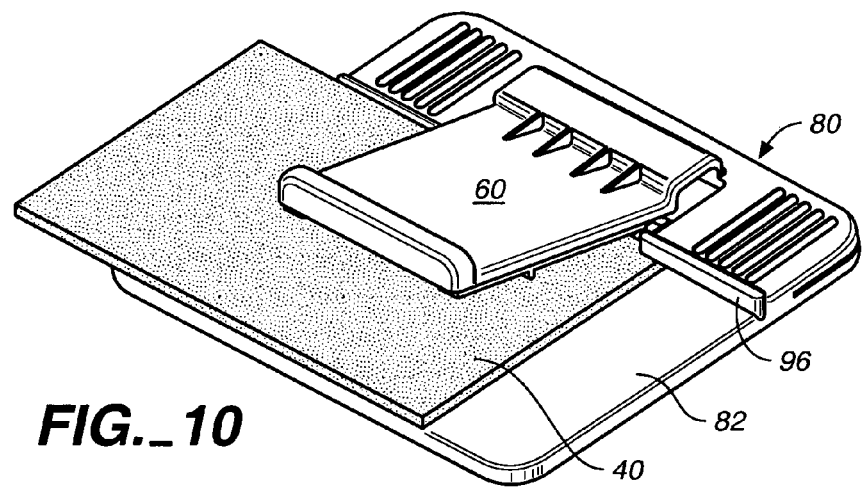
FIG._10
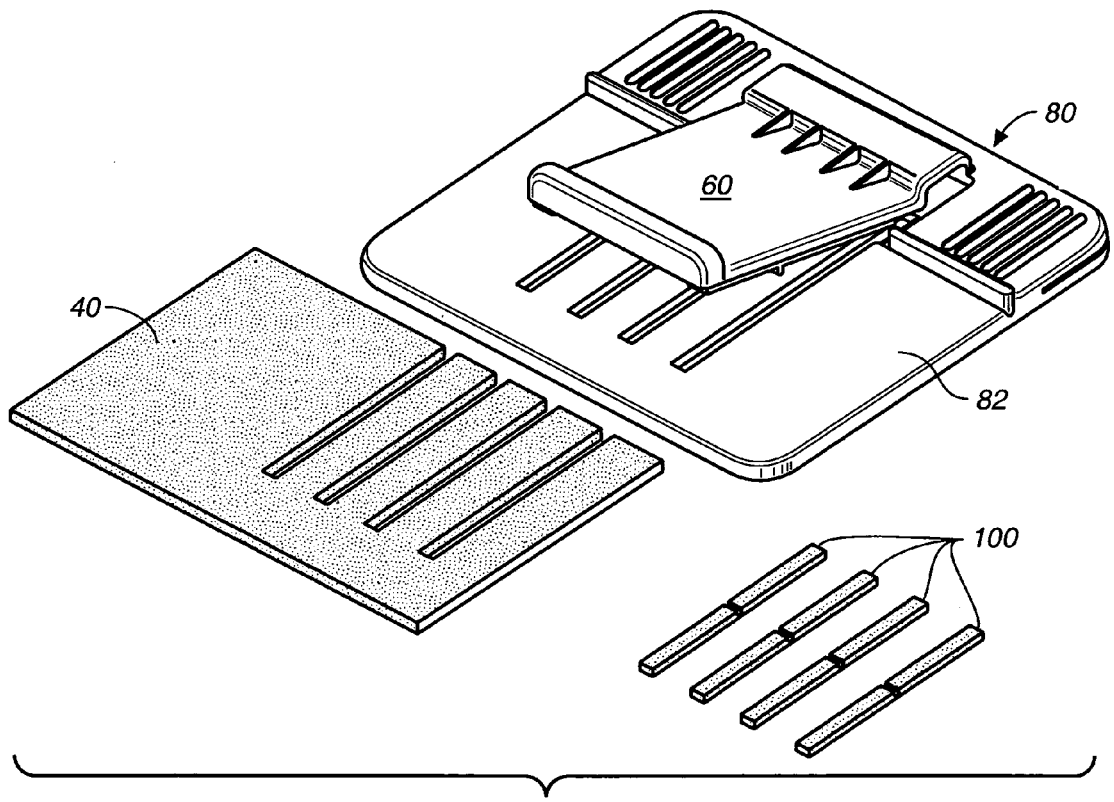
FIG._11

EASY CUTTER

BACKGROUND OF THE INVENTION

This application claims priority to provisional U.S. application Ser. No. 60/200,702 filed Apr. 28, 2000, which is incorporated herein by reference in its entirety.

FIELD OF THE INVENTION

The invention relates to a cutting device for cutting foam sheets, and more particularly, the invention relates to a cutting device for cutting sheets of compressed hemostatic foam.

BRIEF DESCRIPTION OF THE RELATED ART

Bioabsorbable hemostatic foam is used in the medical field to promote hemostasis in many different applications. Two examples of applications in which hemostatic foam is delivered through a cannula are described in International Publication Nos. WO99/56692 and WO99/56632 which are incorporated herein by reference in their entirety. As described in these applications, a pledget of compressed hemostatic foam is cut from a sheet of the foam material and is rolled or folded into a configuration which is inserted into a delivery device. Once the foam pledget is inserted into the delivery device, the foam is hydrated and delivered to a body for promoting hemostatis.

Cutting the compressed hemostatic foam (such as Pharmacia Upjohn Gelfoam) is difficult and awkward. Although cutting the foam with a template and a cutting device, such as a knife is possible, it would be desirable to have a cutting device that can quickly and easily cut a piece of foam of a predetermined size and shape.

SUMMARY OF THE INVENTION

The present invention relates to a cutting device for cutting shapes from sheets of material, such as sheets of compressed hemostatic foam. The present invention also relates to a kit for delivering hemostatic foam including a cutting device.

In accordance with one aspect of the present invention, a cutting device includes a base having an opening with cutting edges; and a flap articulated with respect to the base, the flap having a shape corresponding to the opening and cutting edges corresponding to the cutting edges of the opening.

In accordance with another aspect of the present invention, a cutting device includes a base having an opening with cutting edges; a flap articulated with respect to the base, the flap having a shape corresponding to the opening and cutting edges corresponding to the cutting edges of the opening; and wherein the base is mounted on a card, and the card supports a medical device system.

In accordance with further aspect of the present invention, a medical kit includes a sheet of medical foam material; and a cutter for cutting the foam material, the cutter includes a base having an opening with cutting edges, and a flap articulated with respect to the base for cutting foam.

In accordance with another aspect of the present invention, a kit for cutting sheets of material, the kit including a base having an opening with cutting edges; a flap articulated with respect to the base, the flap having a shape corresponding to the opening and cutting edges corresponding to the cutting edges of the opening; and a presentation card which supports at least one medical device.

In accordance with a further aspect of the present invention, a method of cutting foam sheets includes the steps of placing a piece of foam underneath an articulate edge of a cutting device; and pushing down the articulated edge to cut the piece of foam between the edges of the articulated flap and an edge of an opening on a base of the cutting device.

In accordance with another aspect of the present invention, a medical system includes a sheet of medical foam material; and a cutter for cutting the foam material, the cutter including a base having an opening with cutting edges, and a flap articulated with respect to the base for cutting foam.

The present invention provides a cutting device that can quickly and easily cut a piece of foam to a predetermined size and shape.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 1 is a perspective view of a first embodiment of an easy cutter according to the present invention;

FIG. 2 is a perspective view of step 1 with the easy cutter of FIG. 1;

FIG. 3 is a perspective view of step 2 with the easy cutter of FIG. 1;

FIG. 4 is a perspective view of a second embodiment of an easy cutter according to the present invention;

FIG. 5 is a perspective view of step 1 with the easy cutter of FIG. 4;

FIG. 6 is a perspective view of step 2 with the easy cutter of FIG. 4;

FIG. 7 is a perspective view of the easy cutter of FIG. 4. connected to a presentation card for medical device systems;

FIG. 8 is a perspective view of an easy cutter according to a third embodiment of the invention;

FIG. 9 is a perspective view of a top portion of the easy cutter of FIG. 8 in an inverted configuration;

FIG. 10 is a perspective view of step 1 with the easy cutter of FIG. 8; and

FIG. 11 is a perspective view of step 2 with the easy cutter of FIG. 8.

DETAILED DESCRIPTION OF THE PREFERRED EMBODIMENTS

The easy cutter 10 of FIG. 1 is formed from a sheet of rigid material such as polypropylene with a rigidity which is sufficient to cut, shear, and/or punch through the foam material. The polypropylene or other sheet has a U-shaped cut which forms an articulated flap 30 for cutting the foam. As shown in FIG. 2, a sheet of hemostatic material is inserted under the articulated flap and the flap is pushed down to cut the foam between the edges of the articulated flap and the edges of the U-shaped opening. The material may be cut by shearing, punching, or a combination thereof. FIG. 3 illustrates a cut piece of foam 20 which has been cut from a sheet 40 of foam material. The easy cutter 10 may be incorporated as part of a presentation card which supports a medical device system for delivering the cut foam material.

FIGS. 4–6 illustrate an alternative embodiment of an easy cutter 50 including a base 52 and a flap 60. The easy cutter 50 of FIG. 4 may be molded out of a plastic material. The flap 60 includes a cutting edge which corresponds to an opening 51 in the base 52. The opening 51 of FIG. 4 is shown having three flat side portions 53. A guide edge 62 is also provided for aligning a sheet of foam material. The guide edge 62 is oriented along a guide plane that intersects two of the opening flat side portions 53. As shown in FIG. 5, the sheet of foam 40 is inserted below the flap 60 so that an edge surface of the foam 40 is aligned with the guide edge 62. The flap 60 is pushed downward cutting a piece 20 of foam of a predetermined size and shape. FIG. 7 illustrates the easy cutter 50 which has been mounted on a card 70 which supports a medical device system for delivering the cut foam material. The easy cutter 50 may be formed from two pieces which are snapped together to trap the card 70 between the pieces.

FIG. 8 illustrates an alternative embodiment of an easy cutter 80 which cuts four strips of foam material from a foam sheet. The easy cutter 80 of FIG. 8 includes a base 82 having four openings and a flap 90 having four rails 92 for cutting the four strips of foam. Each of the rails 92 includes a ridge 94 (shown in FIG. 9) which forms a crease in the foam material. The creases may be particularly useful for folding the strip of foam material at a predefined location. As shown in FIG. 10, the sheet of hemostatic foam material 40 is inserted into the easy cutter and abuts the guide surface 96. The flap 60 is then pressed down to cut the four foam strips 100 shown in FIG. 11.

It should be understood that the easy cutter according to the present invention may be used to cut any number of different shaped pieces of foam. The pieces which are cut may be cut on three sides as illustrated. Alternatively, the easy cutter may cut shapes which require cutting on 1, 2, 3, 4, or more sides of the shape. Other free form shapes such as stars and other polygons may also be cut depending on the particular application.

The easy cutter according to the present invention is particularly designed to be used in a kit including medical devices for delivery of a hemostatic sponge material. However, it should be understood that the easy cutter may also be used for cutting many different materials in both medical and non-medical applications.

When the easy cutter is used for medical applications it is a sterile single use device or a device which may be cleaned, resterilized, and reused. For non-medical applications the easy cutter may be unsterilized.

The term foam as used herein is intended to mean a biocompatible material which is capable of being hydrated and is resiliently compressible in a hydrated state. Preferably, the foam is non-immunogenic and may be absorbable or non-absorbable.

While the invention has been described in detail with reference to the preferred embodiments thereof, it will be apparent to one skilled in the art that various changes and modifications can be made and equivalents employed, without departing from the present invention.

What is claimed is:

1. A medical kit comprising:
   a sheet of hemostatic material having an edge surface;
   a hemostatic material delivery device; and
   a device for cutting at least one pledget from the sheet of hemostatic foam material, wherein the pledget is shaped for insertion into the hemostatic material delivery device, the cutting device including:
   a base defining a first opening having at least two flat side portions, the first opening being sized to form the pledget;
   a guide stop associated with the base and adapted to engage the hemostatic material edge surface, the guide stop being aligned along a guide plane that intersects the at least two flat side portions; and
   a flap articulated with respect to the base and including a first cutting edge sized to correspond to the first opening.

2. The kit of claim 1, in which the base includes a second opening having at least two flat side portions, in which the guide plane further intersects the two flat side portions of the second opening, and in which the flap includes a second cutting edge sized to correspond with the second opening, thereby to cut a second pledget from the sheet of hemostatic material.

3. The kit of claim 1, further comprising a ridge extending from the flap and toward the opening.

4. The kit of claim 1, in which the hemostatic material comprises a hemostatic foam, and the base and flap are formed of a material suitable fox cutting the hemostatic foam.

5. The kit of claim 1, in which the base and flap are formed of a molded plastic material.

6. The kit of claim 1, in which the guide stop comprises a guide edge projecting from the base.

* * * * *